US006387045B1

(12) United States Patent
Takahashi

(10) Patent No.: US 6,387,045 B1
(45) Date of Patent: May 14, 2002

(54) FLOW RATE CONTROLLER FOR AN ENDOSCOPE PIPE

(75) Inventor: Kazuaki Takahashi, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/414,716

(22) Filed: Oct. 12, 1999

Related U.S. Application Data

(62) Division of application No. 09/135,018, filed on Aug. 17, 1998, now Pat. No. 6,132,369.

(30) Foreign Application Priority Data

| Aug. 21, 1997 | (JP) | 9-242120 |
|---|---|---|
| Sep. 16, 1997 | (JP) | 9-281398 |
| Sep. 30, 1997 | (JP) | 9-282541 |
| Sep. 30, 1997 | (JP) | 9-282542 |

(51) Int. Cl.$^7$ .................................................. A61B 1/015
(52) U.S. Cl. ................................. 600/159; 600/158
(58) Field of Search ........................... 600/158, 159

(56) References Cited

U.S. PATENT DOCUMENTS

| 4,345,463 A | * | 8/1982 | Wilson et al. ................. 73/190 |
| 4,402,310 A | * | 9/1983 | Kimura ........................ 604/30 |
| 5,318,225 A | * | 6/1994 | Condron ........................ 239/1 |
| 5,402,770 A | * | 4/1995 | Iida et al. .................... 600/159 |
| 5,746,238 A | * | 5/1998 | Brady et al. .................... 137/3 |
| 5,938,589 A | * | 8/1999 | Wako et al. ................. 600/159 |

FOREIGN PATENT DOCUMENTS

| JP | 01297045 A | 11/1989 |
| JP | 01310638 A | 12/1989 |

* cited by examiner

*Primary Examiner*—John P. Leubecker
(74) *Attorney, Agent, or Firm*—Snider & Associates; Ronald R. Snider

(57) ABSTRACT

An endoscope in which the advantage of a pinch valve is used, and the flow rate of fluid can be regulated variably. In an electromagnetic valve unit for carrying out the opening/closing control of pipes in the endoscope, a pinch valve is disposed in a water feed pipe, and a diaphragm valve is disposed in an air feed pipe. Also, for ease of draining work, an air feed pipe is connected to the water feed pipe, an auxiliary valve consisting of a diaphragm valve is disposed, and a check valve is installed. Further, for example, three control pipes with different diameters and three electromagnetic valves for opening/closing these control pipes are provided in each pipe. By carrying out the opening/closing control of these electromagnetic valves by using an operation switch, the flow rate in each pipe in the endoscope is regulated variably. Also, for the suction pipe in the endoscope, by providing, for example, three open-to-atmosphere pipes with different diameters and three electromagnetic valves, the flow rate of the suction pipe can be regulated variably.

9 Claims, 9 Drawing Sheets

FLOW RATE CONTROLLER FOR AN ENDOSCOPE PIPE

This is a divisional application of U.S. patent application Ser. No. 09/135,018, filed Aug. 17, 1998, now U.S. Pat. No. 6,132,369.

BACKGROUND OF THE INVENTION

This application claims the priority of Japanese Patent Application No. 9-242120 filed on Aug. 21, 1997, and Nos. 9-282542 and 9-282541 filed on Sep. 30, 1997, and No. 9-281398 filed on Sep. 16, 1997 which are incorporated herein by reference.

1. Field of the Invention

The present invention relates to an opening/closing controller for opening/closing a pipe such as an air feed pipe, water feed pipe, and suction pipe disposed in an endoscope and a flow rate controller for controlling a flow rate.

2. Description of the Prior Art

FIG. 10 shows a configuration of a conventional endoscope and an electromagnetic valve unit. In FIG. 10, a water feed pipe 2A, an air feed pipe 3A, and a suction pipe (also used as a treatment tool inserting channel) 4A are disposed from a distal end section 1A to an operating section 1B in an endoscope 1, and the suction pipe 4A is connected to a forceps port 5 disposed in the operating section 1B. As shown in FIG. 10, the operating section 1B is provided with an air/water feed (A/W) switch 6, which is a two-stage switch, a suction (SUC) switch 7, and a photographing button 8. The operation control signals of the switches 6 and 7 are supplied to an electromagnetic valve unit 9 via signal lines (not shown). Also, in order to connect the electromagnetic valve unit 9 to the operating section 1B, a water feed pipe 2B, an air feed pipe 3B, and a suction pipe 4B are provided in a cable or the like.

The electromagnetic valve unit 9 is provided with five electromagnetic valves Va, Vb, Vc, Vd and Ve for opening/closing each of the pipe, a pump 62, a control section 63, and a feed water tank 28. The feed water tank 28 is connected to the pump 62 via an air feed pipe 3C, and also connected to the electromagnetic valve Va via a water feed pipe 2C. Further, a suction pipe 4C is connected with a suction tank 29 and a pump.

According to the above-described configuration, when the air/water feed switch 6 is not operated, only the electromagnetic valve Vc is opened. By closing the electromagnetic valves Va and Vc and opening Vb, air is fed to an air feed pipe 3, and by closing the electromagnetic valves Vb and Vc and opening Va, water is fed to a water pipe 2. By this air/water feed, contamination etc. of an objective lens window disposed in the distal end section 1A can be removed. Also, by closing the electromagnetic valve Ve and opening Vd, suction is effected, whereby the content etc. in a body being observed are sucked and discharged via a suction pipe 4. It is to be noted that endoscope systems controlling the fluid by using the above-mentioned electromagnetic valves have been disclosed in Unexamined Japanese Patent Application Laid-Open Nos. 1-297045, 1-310638, etc.

As the above-mentioned electromagnetic valves Va through Ve, a pinch valve, for example, is used. This pinch valve closes the pipe by crushing the soft pipe portion of each pipe arranged in the valve, and opens it by releasing the crushed state. Such a pinch valve has an advantage that an opening/closing portion is not clogged with dirt etc., and a cleaning brush can be caused to pass through a valve portion, so that the pipe inside can be cleaned easily.

BRIEF SUMMARY OF THE INVENTION

OBJECT OF THE INVENTION

However, the pinch valve has a problem in that the soft pipe becomes liable to be crushed, or the deterioration in the soft pipe is accelerated because the soft pipe is crushed. Also, as comparing with a diaphragm valve, the pinch valve consumes much electric power because it is an electromagnetic valve, and its cost is high considering the replacement work etc., resulting from the deterioration in the soft pipe.

Although the opened/closed pipes carry various fluids as described above, the air feed pipe has a little need especially for periodic cleaning unless a liquid etc. enter. Therefore, if the air feed pipe is not cleaned and accordingly no pinch valve is disposed, the above-mentioned disadvantage can be reduced.

The present invention was made to solve the above problems, and accordingly a first object thereof is to provide an opening/closing controller for an endoscope pipe in which the advantage of cleaning properties of a pinch valve is used, the disadvantage of the pinch valve is reduced by restricting the application locations thereof, and the power consumption and the cost can be decreased.

Also, in the fluid control of the above-mentioned endoscope pipe, only the control as to whether or not air feed, water feed, or suction is executed is carried out, and the quantities of fed air, fed water, and suction cannot be regulated variably at the present. In the air/water feed to the aforesaid objective lens window, if the quantity can be regulated variably, the contamination can be removed efficiently while considering the effect on the inside of a body being observed and the like. Also, in the suction of the content, if the quantity can be regulated variably, the content can be discharged according to the situation. As a result, an endoscope which is easy to use can be obtained.

The present invention was made to solve the above problems, and accordingly a second object thereof is to provide a flow rate controller for an endoscope pipe in which the flow rate of a fluid in the pipe can be regulated variably, thereby obtaining an endoscope which is easy to use.

SUMMARY OF THE INVENTION

To achieve the above first object, the opening/closing controller for an endoscope duct in accordance with the present invention is characterized by comprising: an air feed pipe, which is provided in an endoscope, for feeding air; a liquid pipe, which is provided in an endoscope, for feeding a liquid; a diaphragm valve provided as an opening/closing valve for the air feed pipe; a check valve, which is provided in the air feed pipe, for preventing a liquid from entering from the outside; and a pinch valve provided as an opening/closing valve for the liquid pipe.

According to the above configuration, since the reverse flow of water etc. to the air feed pipe can be prevented at the check valve, the air feed pipe is not contaminated by a fluid other than air, so that the air feed pipe need not be cleaned. If the diaphragm valve is disposed in the air feed pipe, the power consumption and the cost can be decreased. In the mean time, for the water feed pipe and suction pipe, since a pinch valve is used, a cleaning brush can be used, and other advantages regarding the cleaning properties can be enjoyed.

Also, another invention is characterized in that the air feed pipe is connected to the liquid pipe via a check valve, and there is provided an auxiliary opening/closing valve, consisting of a diaphragm valve, for supplying air from the air feed pipe to the liquid pipe. According to this configuration, the air feed pipe is connected to the water feed pipe by opening the auxiliary opening/closing valve, so that air can be fed to the water feed pipe, whereby draining work can be performed easily.

Further, to achieve the second object, the flow rate controller for an endoscope pipe in accordance with the present invention is characterized by comprising: various pipes provided in an endoscope; a plurality of control pipes with different pipe diameters connected to the pipe in a branching state; an opening/closing valve for opening/closing each of the plural control pipes; and a control section for variably regulating the flow rate in the pipe by selective opening/closing control of the plural opening/closing valves.

In the above configuration, the flow rate can be regulated variably by the combined use of the plural control pipes on the basis of the control of the plural opening/closing valves.

An operation switch for regulating the flow rate may be disposed on the side of a fluid control unit separate from the endoscope, or may be disposed in an operating section of the endoscope.

According to the above configuration, the plural control pipes with different diameters are disposed for one of the endoscope pipe such as the air feed pipe and water feed pipe. When, for example, three control pipes are provided, the flow rate changes depending on which of the three control pipes is opened by the opening/closing valve, and also the flow rate changes according to the combination of opened pipes.

This flow rate regulating operation, that is, the setting of which of the opening/closing valves is opened, is performed by using a selecting switch etc. provided on a control panel etc. on the side of the fluid control unit. Also, the flow rate regulating operation can be executed by using the operation switch in the operating section of the endoscope. In this case, the flow rate regulation by the control pipes with different diameters is made possible by opening/closing a predetermined opening/closing valve according to the pressing pressure or stroke amount of the operating section.

Also, the flow rate controller for an endoscope pipe in accordance with another invention is characterized by comprising: a suction pipe provided in an endoscope; a plurality of open-to-atmosphere pipes connected to the suction pipe in a branching state; an opening/closing valve for opening/closing each of the plural open-to-atmosphere pipes; and a control section for variably regulating the flow rate in the suction pipe by selective opening/closing control of the plural opening/closing valves.

Pipes with different inside diameters can be used as the plural open-to-atmosphere pipes, and the flow rate can be regulated variably by the combined use of the plural open-to-atmosphere pipes on the basis of the control of the plural opening/closing valves.

An operation switch for regulating the flow rate in the suction pipe may be disposed on the side of a fluid control unit separate from the endoscope, or may be disposed in an operating section of the endoscope.

According to the above configuration, the plural open-to-atmosphere pipes are disposed for one suction pipe, so that the suction flow rate changes depending on how many open-to-atmosphere pipes are opened by the opening/closing valve. If these open-to-atmosphere pipes have different diameters, the flow rate changes depending on which of the pipes is opened by the opening/closing valve, and also the flow rate changes according to the combination of opened pipes.

DETAILED DESCRIPTION OF THE PREFERRED EMBODIMENTS

First Embodiment

Figure 1:
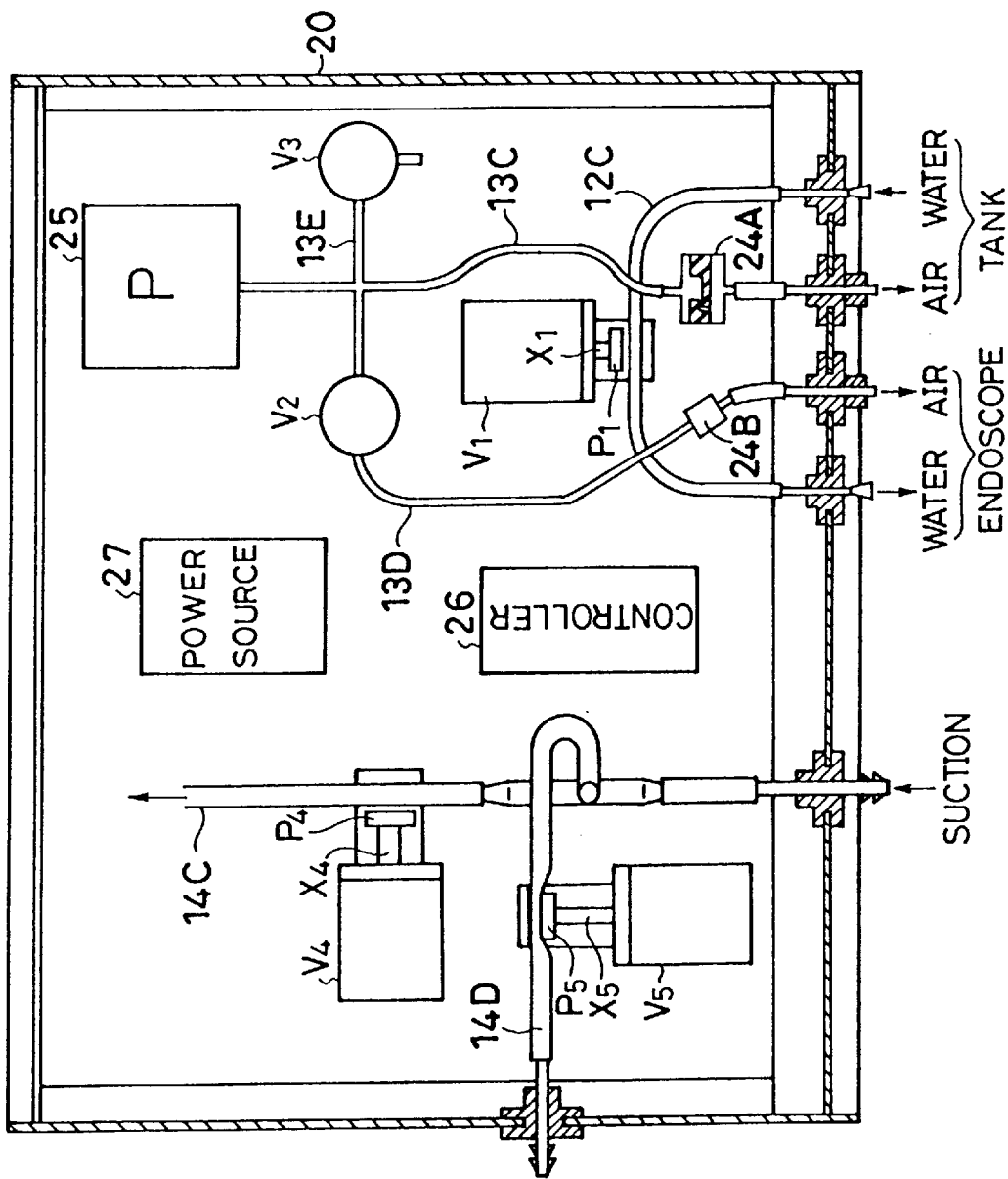
FIG. 1 is a schematic view showing a configuration of an opening/closing controller (electromagnetic valve unit) for an endoscope pipe in accordance with a first embodiment of the present invention.
Figure 2:
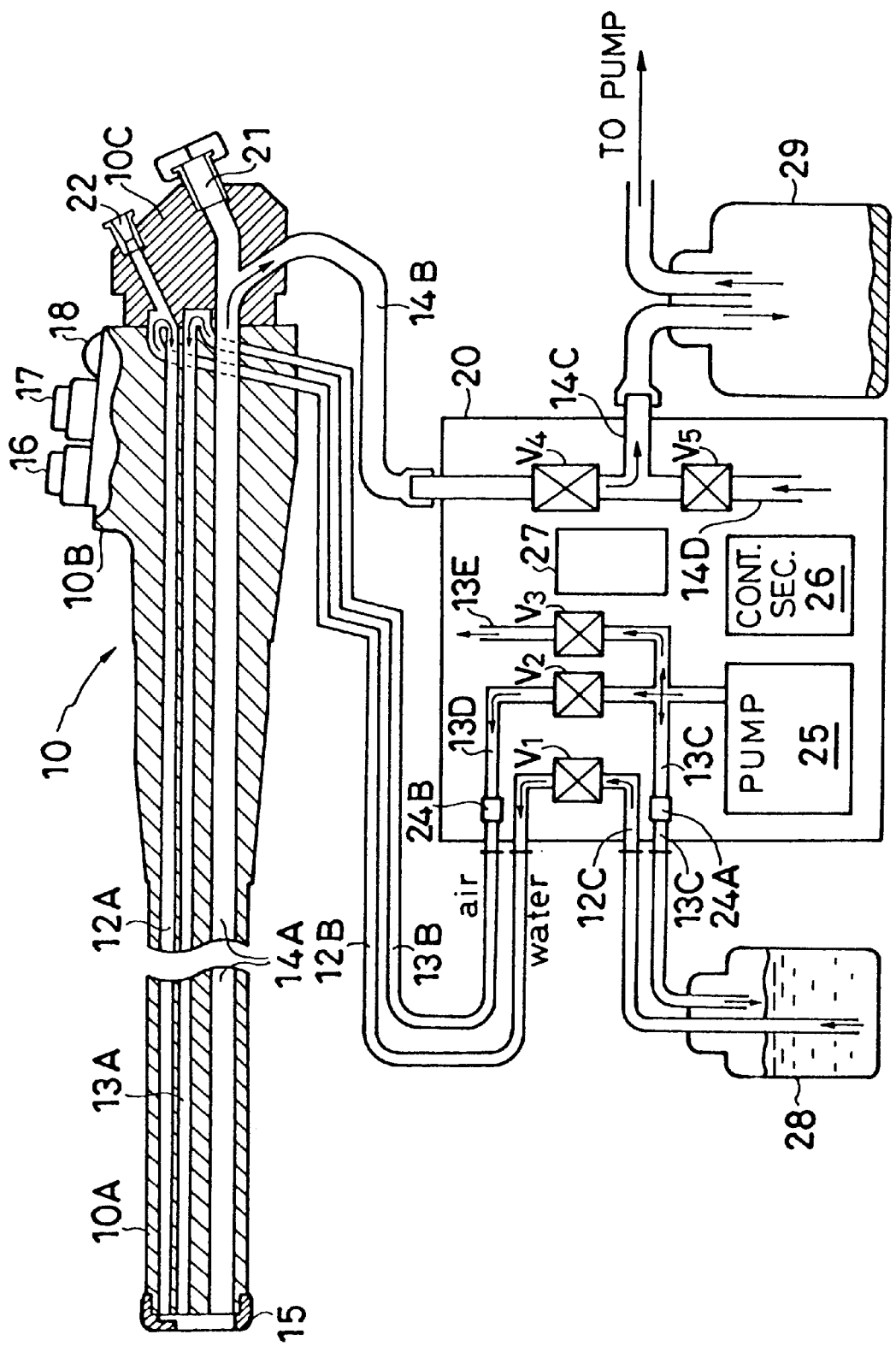
FIG. 2 is a schematic view showing the whole configuration of an endoscope in which the electromagnetic valve unit of the first embodiment is used.

FIG. 1 shows a configuration of an electromagnetic valve unit, which is an opening/closing controller for an endoscope pipe, in accordance with a first embodiment, and FIG. 2 shows the whole configuration of an endoscope pipe system. First, the configuration of the endoscope pipe system will be explained. Referring now to FIG. 2, an endoscope (electronic endoscope) 10 is provided with a water feed pipe 12A, an air feed pipe 13A, and a suction pipe (also used as a treatment tool inserting channel) 14A are disposed from a distal end section 10A to an operating section 10B. To a distal end of the distal end section 10A is installed a removable cap 15, and the cap 15 is provided with a nozzle etc. for feeding air/water to an observation window (lens window of objective optical system).

As shown in FIG. 2, the operating section 10B is provided with an air/water feed (A/W) switch 16, which is a two-stage switch, a suction (SUC) switch 17, and a photographing button 18. The operation control signals of the switches 16 and 17 are supplied to an electromagnetic valve unit 20 via signal lines (not shown). Also, in order to connect the electromagnetic valve unit 20 to the operating section 10B, a water feed pipe 12B and an air feed pipe 13B are provided in a cable. On the rear side of the operating section 10B there is provided a pipe unit 10C, and the water feed pipe 12A is connected to the water feed pipe 12B and the air feed pipe 13A is connected to the air feed pipe 13B by a folding section formed when the pipe unit 10C is connected.

The pipe unit 10C is fitted with a suction pipe 14B extending to the electromagnetic valve unit 20, and the suction pipe 14B is provided with a forceps port 21 separating from the halfway. It is to be noted that a member 22 shown in the figure, which is connected to the aforesaid water feed pipe 12A, is a lens surface flushing port for feeding air/water by mounting a syringe or the like when the degree of contamination of an observation window lens surface is high.

The electromagnetic valve unit 20 is provided with a water feed pipe 12C, air feed pipes 13C, 13D and 13E, suction pipes 14C and 14D, first to fifth valves V1, V2, V3, V4 and V5 for controlling opening/closing of these pipes, check valves 24A and 24B, a pump 25, control section 26, and a power source 27. Also, the electromagnetic valve unit 20 is connected with a feed water tank 28 and a suction tank 29, and the suction tank 29 is connected to another pump.

FIG. 1 shows a detailed configuration of the electromagnetic valve unit 20. The water feed pipe 12C is fitted with a first valve V1, and a pinch valve (electromagnetic valve) is disposed as the first valve V1. The air feed pipe 13C connected to the pump 25 is connected to the feed water tank 28, and the check valve 24A is installed on the exit side of the air feed pipe 13C to prevent the reverse flow of liquid. The air feed pipe 13D branching from the air feed pipe 13C is connected to the side of the endoscope, and the second valve V2 is disposed in the air feed pipe 13D, and a check valve 24B is installed on the exit side of the air feed pipe 13D.

Further, the open-to-atmosphere pipe 13E branching from the air feed pipe 13C is provided, and the third valve V3 is disposed in this open-to-atmosphere pipe 13E. This open-to-atmosphere pipe 13E serves to discharge air from the pump 25 to the atmosphere in the standby state of air/water feed. As the valves V2 and V3, diaphragm valves are disposed. The diaphragm valve V2, V3, which performs opening/closing operation by electrically driving a diaphragm, can be driven by a lower electric power than the electromagnetic valve system.

In the mean time, the suction pipe 14C is provided with the fourth valve V4, and the atmosphere suction pipe 14D branching from the suction pipe 14C is provided with the fifth valve V5. This atmosphere suction pipe 14D serves to introduce air in the atmosphere into the suction tank 29 to operate the pump in the standby state of suction. As the valves V4 and V5, pinch valves (electromagnetic valves) are disposed like the first valve V1. The pinch valve V1, V4, V5 drives a pressing section P1, P4, P5 installed to a drive shaft X1, X4, X5 by using an electromagnetic solenoid etc., by which a soft section disposed in the valve is crushed to close the pipe.

The following is a description of the operation of this embodiment configured as described above. When the water feed operation is performed by means of the air/water switch 16 in the operating section 10B shown in FIG. 2, in the electromagnetic valve unit 20 shown in FIG. 1, the first valve V1 is opened, and the second and third valves V2 and V3 are closed in a state in which the pump 25 is operated, so that water is fed via the water feed pipes 12C and 12B and the water feed pipe 12A. Also, when the air feed operation is performed by means of the switch 16, the first and third valves V1 and V3 are closed, and the second valve V2 is opened, so that the air is fed via the air feed pipes 13D and 13B and the air feed pipe 13A. In the standby state of air/water feed, only the third valve V3 is opened, so that the air from the pump 25 is discharged to the atmosphere through the open-to-atmosphere pipe 13E.

In the air feed pipes 13C and 13D, the presence of the check valves 24A and 24B prevents water etc. from flowing reversely and entering the pipes. Specifically, the endoscope is configured so that the water feed pipe 12A and the air feed pipe 13A are joined together on the distal end side, so that water may flow reversely from this portion. Also, when an external air feed pipe is removed from a connector of the electromagnetic valve unit 20, water etc. may enter. In such cases, the entrance of liquid can be prevented.

Further, when the suction switch 17 in the operating section 10B is operated, as shown in FIG. 1, the fourth valve V4 is opened, and the fifth valve V5 is closed, so that suction is effected via the suction pipes 14C and 14B and the suction pipe 14A. In the standby state of suction, only the fifth valve V5 is opened, so that air is sucked through the atmosphere suction pipe 14D.

In the mean time, when the endoscope is cleaned after use, the first, fourth, and fifth valves V1, V4 and V5, consisting of pinch valves, are opened, by which cleaning is performed by inserting a cleaning brush into the water feed pipe 12C and suction pipes 14C and 14D. For the air feed pipes 13C to 13E in which the second and third valves V2 and V3, consisting of diaphragm valves, are disposed, cleaning need not be performed because the entrance of liquid is prevented by the check valves 24A and 24B.

It is to be noted that for the fifth valve V5 disposed in the atmosphere suction pipe (air feed pipe) 14D, although a pinch valve is used in this embodiment considering the cleaning efficiency because there is a possibility of sucking a contaminated liquid, this fifth valve V5 can also be formed by a diaphragm valve by disposing a check valve.

As described above, according to the first embodiment, the advantage of cleaning properties of pinch valve is used, and the use of the pinch valve having a problem in that a soft pipe becomes liable to be crushed or the deterioration of soft pipe is accelerated can be reduced. Also, the power consumption can be decreased, and a low cost can be achieved.

Second Embodiment

Figure 3:
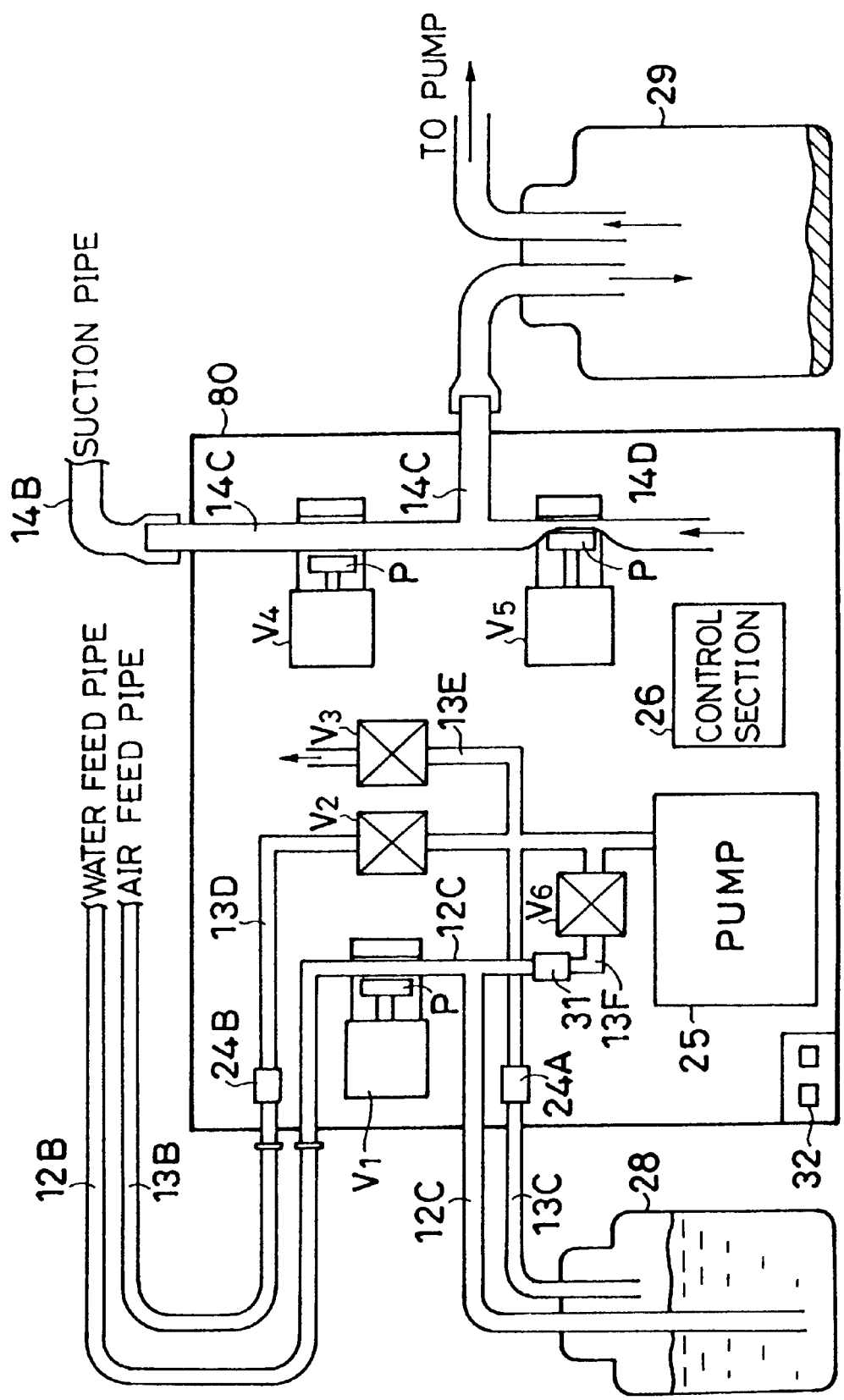
FIG. 3 is a schematic view showing a configuration of an opening/closing controller for an endoscope pipe in accordance with a second embodiment of the present invention.

FIG. 3 shows a configuration of an endoscope fluid controller of a second embodiment, which can perform draining work easily. Specifically, in the water feed pipe and suction pipe in the endoscope, draining is performed by air feed after the use of endoscope or the cleaning of pipes. When draining is performed by feeding air to the water feed pipe by changing the connecting state, for example, by disconnecting the water feed pipe and air feed pipe installed to the electromagnetic valve unit, the work is troublesome, much time is required, and the easiness is deteriorated. The second embodiment improves this point.

Like the first embodiment, an electromagnetic valve unit 80 shown in FIG. 3 is provided with a pump 25 and a control section 26 for carrying out opening/closing control etc. of the electromagnetic valves, and also provided with a feed water tank 28 and a suction tank 29 on the outside. The pump 25 is provided with an air feed pipe 13D communicating with an air feed pipe 13B, and the air feed pipe 13D is provided with a check valve 24B and a diaphragm valve V2. The air feed pipe 13D is connected with an open-to-atmosphere pipe 13E provided with a diaphragm valve V3, and connected with an air feed pipe 13C leading to the feed water tank 28. Also, a check valve 24A is provided in the air feed pipe 13C at the exit of the unit 80. These check valves 24A and 24B prevent the entrance of water etc. from the outside into the air feed pipes 13C, 13D and 13E in the electromagnetic valve unit 80.

Further, there are provided a water feed pipe 12C leading from the feed water tank 28 to a water feed pipe 12B and a pinch valve V1. An air feed pipe 13F communicating with the pump 25 as shown in the figure is connected to an intermediate position of the water feed pipe 12C. This air feed pipe 13F is provided with an auxiliary valve (draining valve) V6, consisting of a diaphragm valve, and a check valve 31. For the suction pipe 14, a suction pipe 14C is provided with a pinch valve V4, and an open-to-atmosphere pipe 14D is provided with a pinch valve V5.

Also, a draining switch 32 for performing the draining work is disposed on the control panel etc. of the electromagnetic valve unit 80, and the signal of this operation switch 32 is given to the control section 26.

The following is a description of the operation of the second embodiment configured as described above. When the water feed operation is performed by means of the air/water switch 16 shown in FIG. 2, in the electromagnetic valve unit 80 shown in FIG. 3, the valves V2, V3 and V6 are closed, and the valve V1 is opened in a state in which the pump 25 is operated, so that water is fed via the water feed pipes 12C and 12B and the water feed pipe 12A. Also, when the air feed operation is performed by means of the switch 16, the valves V3, V1 and V6 are closed, and the valve V2 is opened, so the air is fed via the air feed pipes 13D and 13B and the air feed pipe 13A.

In this embodiment, air can be fed to the water feed pipe 12. Specifically,when the draining switch 32 is turned on, the control section 26 closes the valves V2 and V3 and opens the valve V1, and opens the auxiliary valve V6, by which the air from the pump 25 is supplied to the water feed pipes 12C and 12B and the water feed pipe 12A. Thereby, the draining work in the feed pipe (duct) 12 can be performed easily by a pressing operation of the switch 32, and the work for attaching and detaching the pipes, which has been needed conventionally, is unnecessary. In the above-mentioned operation, the check valve 31 prevents the reverse flow of water into the air feed pipe 13F.

Thus, according to the second embodiment, the draining work can be performed easily without disconnecting the pipes. It is to be noted that although the draining of the water feed pipe is explained in the above-described second embodiment, the same configuration can be used in the suction pipe.

Third Embodiment

Figure 4:
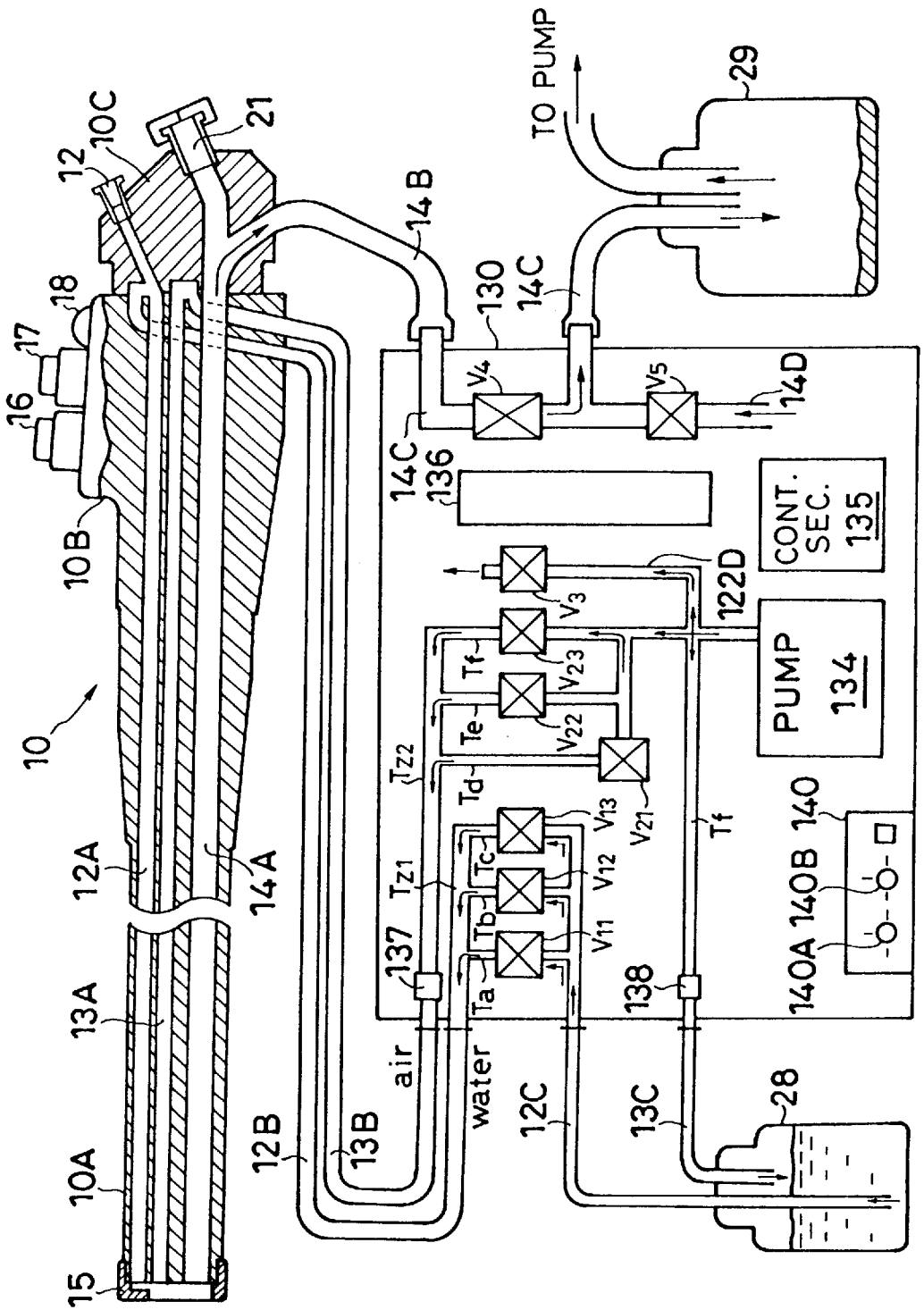
FIG. 4 is a schematic view showing a configuration of a flow rate controller for an endoscope pipe in accordance with a third embodiment of the present invention.
Figure 5:
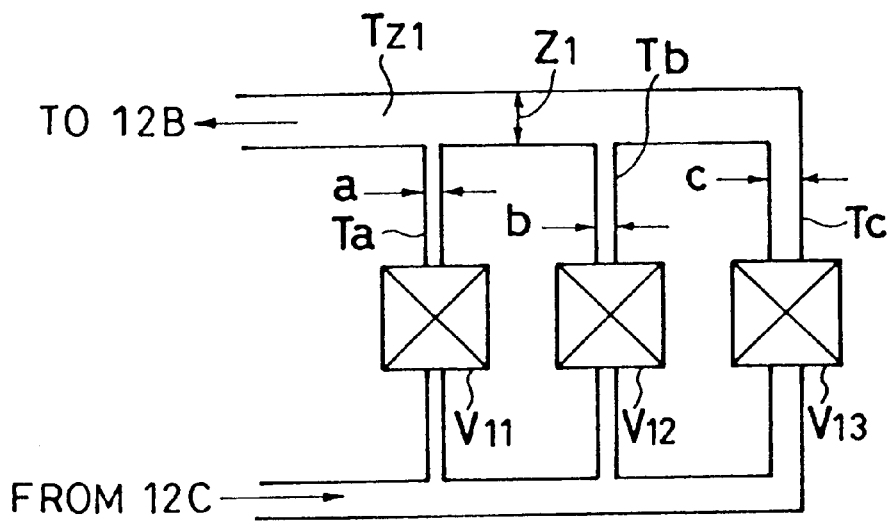
FIG. 5 is a schematic view showing a configuration for controlling the flow rate of a water feed pipe shown in FIG. 4.
Figure 6:
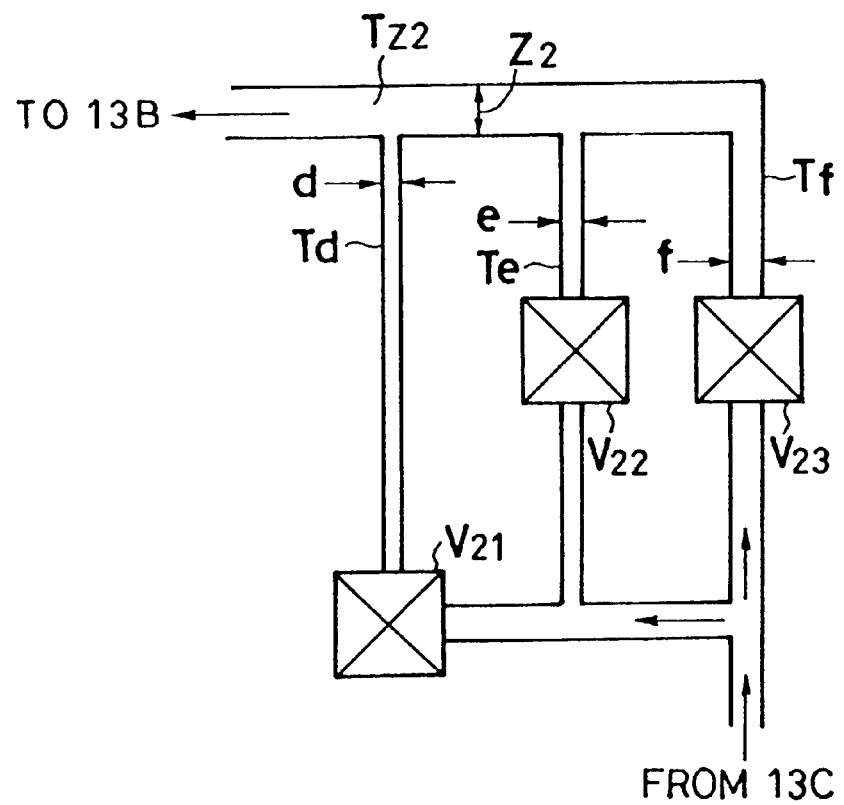
FIG. 6 is a schematic view showing a configuration for controlling the flow rate of an air feed pipe shown in FIG. 4.

FIGS. 4 to 6 show a configuration of a flow rate controller for an endoscope pipe in accordance with a third embodiment. As shown in FIG. 4, the configuration of an endoscope (electronic endoscope) 10 is the same as that of the first embodiment. A pipe unit 10C is installed to an operating section 10B, and an electromagnetic valve unit 130 is connected to a water feed pipe 12B, an air feed pipe 13B, and a suction pipe 14B.

The electromagnetic valve unit 130 is provided with a pump 134, a control section 135, and a power source 136, and also is connected with a feed water tank 28 and a suction tank 29. Also, in order to carry out the flow rate control of the water feed pipe 12, the electromagnetic valve unit 130 is provided with control pipes Ta, Tb and Tc and electromagnetic valves V11, V12 and V13. Specifically, as shown in FIG. 5, the pipe To with the largest diameter (inside diameter) c is installed so as to connect the water feed pipe 12B to a water feed pipe 12C on the side of the feed water tank 28, and the electromagnetic valve V13 for opening/closing the pipe is disposed in this pipe Tc. The pipe Tb with a diameter of b and the pipe Ta with a diameter of a, the diameter being decreased in that order (a<b<c), are provided in parallel to the pipe Tc, and the electromagnetic valves V12 and V11 are disposed in the pipes Tb and Ta, respectively.

In this embodiment, a pipe Tz1, shown in the figure, on the endoscope side is formed so that the diameter z1 thereof is larger than the diameter of the largest pipe Tc (12C) on the tank side. Specifically, taking the reference flow rates (flow rate at the reference supply amount) of the pipes with the diameter a, b, c and z1 as Ha, Hb, Ho and Hz1, the pipes are formed so that Hz1≧Ha+Hb+Hc. Also, the configuration is not as described above, but may be such that the pipes Ta, Tb and Tc may be connected separately to individual tanks 14 and pumps 34.

In the mean time, in order to carry out the flow rate control of the air feed pipe 13, as shown in FIG. 6, there are provided control pipes Td, Te and Tf and electromagnetic valves V21, V22 and V23 for opening/closing these pipes Td, Te and Tf. In this case, the pipe Tf is connected to the air feed pipe 13B via a reverse flow preventive valve 137, and connected to an air feed pipe 13C on the side of the feed water tank 28 via a reverse flow preventive valve 138. These reverse flow preventive valves 137 and 138 prevent the reverse flow of water etc. into the electromagnetic valve unit 130, and thereby prevent the contamination of inside pipes. The pipes Td, Te and Tf have a diameter of d, e and f, respectively, which increases in that order (d<e<f).

Also, the diameter z2 of a pipe Tz2 on the endoscope side is made larger than the diameter of the pipe 13C on the supply side, and taking the reference flow rates (flow rate at the reference supply amount) of the pipes with the diameter d, e, f and z2 as Hd, He, Hf and Hz2, the pipes are formed so that Hz2≧Hd+He+Hf. It is to be noted that the configuration may be such that the pipes Td, Te and Tf are connected separately to the pump 134. Further, as shown in FIG. 4, there are provided an open-to-atmosphere pipe 122D branching from the pipe Tf and an electromagnetic valve V3.

Also, a flow rate regulating switch section 140 for regulating the flow rate of air and water is provided on the control panel of the electromagnetic valve unit 130. By the operation of a water flow rate switch 140A and an air flow rate switch 140B in the flow rate regulating switch section 140, the flow rate of each pipe can be controlled in a stepwise manner.

The following is a description of the operation of the third embodiment configured as described above. When the air/water feed switch 16 is not operated, only the electromagnetic valve V3 is opened. However, when the water feed operation (for example, first pressing) is performed by using the air/water feed switch 16, the electromagnetic valves V21, V22, V23 and V3 are closed, and the opening/closing control of the electromagnetic valves V11, V12 and V13 is carried out so that the flow rate becomes a value set in the flow rate regulating switch section 140.

In this embodiment, since the control pipes Ta, Tb and Tc with three different diameters are used, taking the reference flow rates of the pipes Ta, Tb and Tc as Ha, Hb and Hc, seven stages of flow rates of, for example, Ha<Hb<Hc<Ha+Hb<Ha+Hc<Hb+Hc<Ha+Hb+Hc (other magnitude relationships may be used) can be set including the combination of pipes. Therefore, if only the electromagnetic valve V11 is opened, the minimum flow rate is set, while if all of the electromagnetic valves V11, V12 and V13 are opened, the maximum flow rate is set.

Also, when the water feed operation (for example, second pressing) is performed by using the air/water feed switch 16, the electromagnetic valves V11, V12, V13 and V3 are closed, and the opening/closing control of the electromagnetic valves V21, V22 and V23 is carried out. In this case, as in the above-mentioned case, taking the reference flow rates of the pipes Td, Te and Tf as Hd, He and Hf, seven stages of flow rates of, for example, Hd<He<Hf<Hd+He<Hd+Hf<He+Hf<Hd+He+Hf can be set including the combination of pipes.

Figure 7:
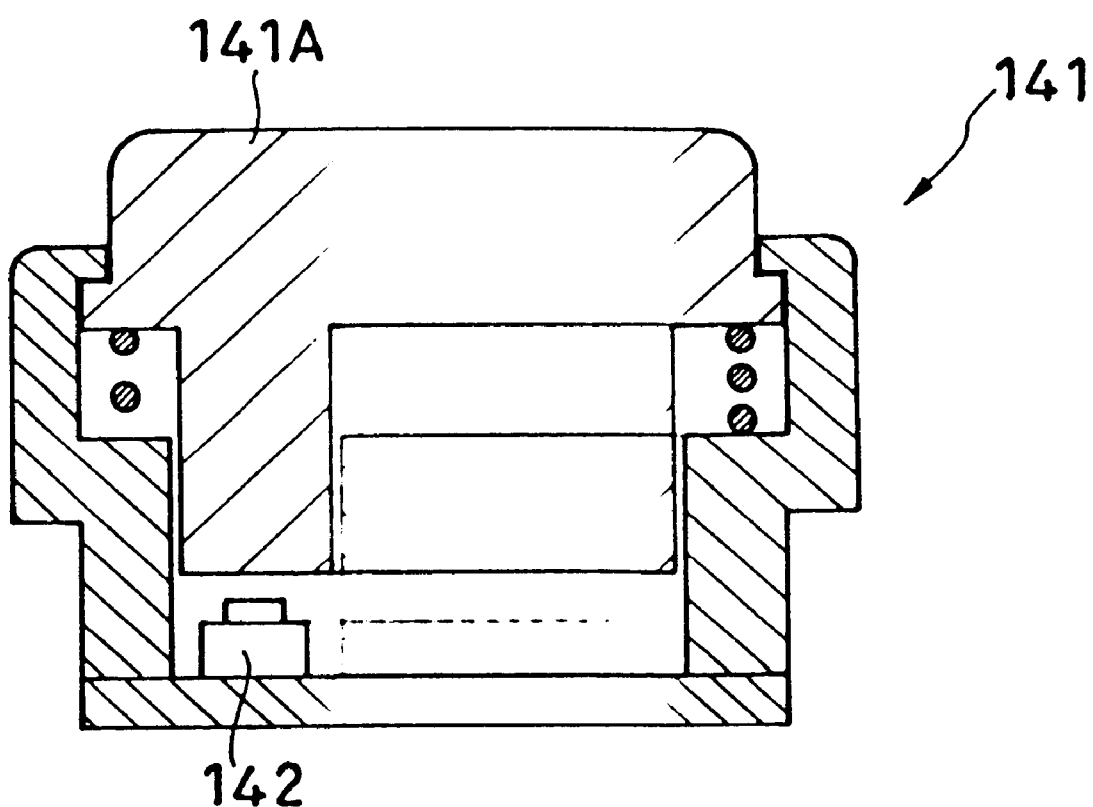
FIG. 7 is a sectional view showing a configuration of an operation switch, which is disposed in an operating section of endoscope, for regulating the flow rate.

FIG. 7 shows a configuration of an operation switch, which is disposed in the operating section 10B of endoscope, for regulating the flow rate. Although the flow rate of air or water is set by the flow rate regulating switch section 140 disposed in the electromagnetic valve unit 130 in the third embodiment, the flow rate regulating operation can be performed by an operation switch 141 shown in FIG. 7, which is disposed in the operating section 10B of endoscope as the air feed switch, water feed switch, and the like.

As shown in FIG. 7, the operation switch 141 is configured so as to press a pressure-sensitive sensor 142 by using a vertically moving operating body (pushbutton section) 141A. As the pressure-sensitive sensor 142 there can be used a pressure-sensitive diode, pressure-sensitive transistor, piezo-type micromachine silicon element, or the like. According to this configuration, the pressing force of the operating body 141A is detected in a stepwise value, and the opening/closing of the electromagnetic valves V11, V12, V13, V21, V22 and V23 is controlled according to this stepwise operating pressure, by which the flow rate can be regulated variably in a stepwise manner. Also, the operation switch 141 may stepwise detect the operation stroke amount, not the pressure. The flow rate can be regulated by this stepwise stroke amount.

Further, although the flow rate regulation of water or air has been explained in this embodiment, needless to say, the above-mentioned configuration can be applied to the flow rate regulation of suction.

As described above, according to the third embodiment, the fluid flow rate in the pipe can be regulated variably, so that in the case of air/water feed operation, contamination can be removed efficiently while considering the effect on the inside of a body being observed and the like, and the discharge of content according to the situation is enabled by the suction operation. As a result, an endoscope which is easy to use can be obtained.

Also, by regulating the flow rate by combining plural control pipes, the flow rate can be set finely, and further the flow rate control can be carried out easily by using the operation switch in the operating section of endoscope.

Fourth Embodiment

Figure 8:
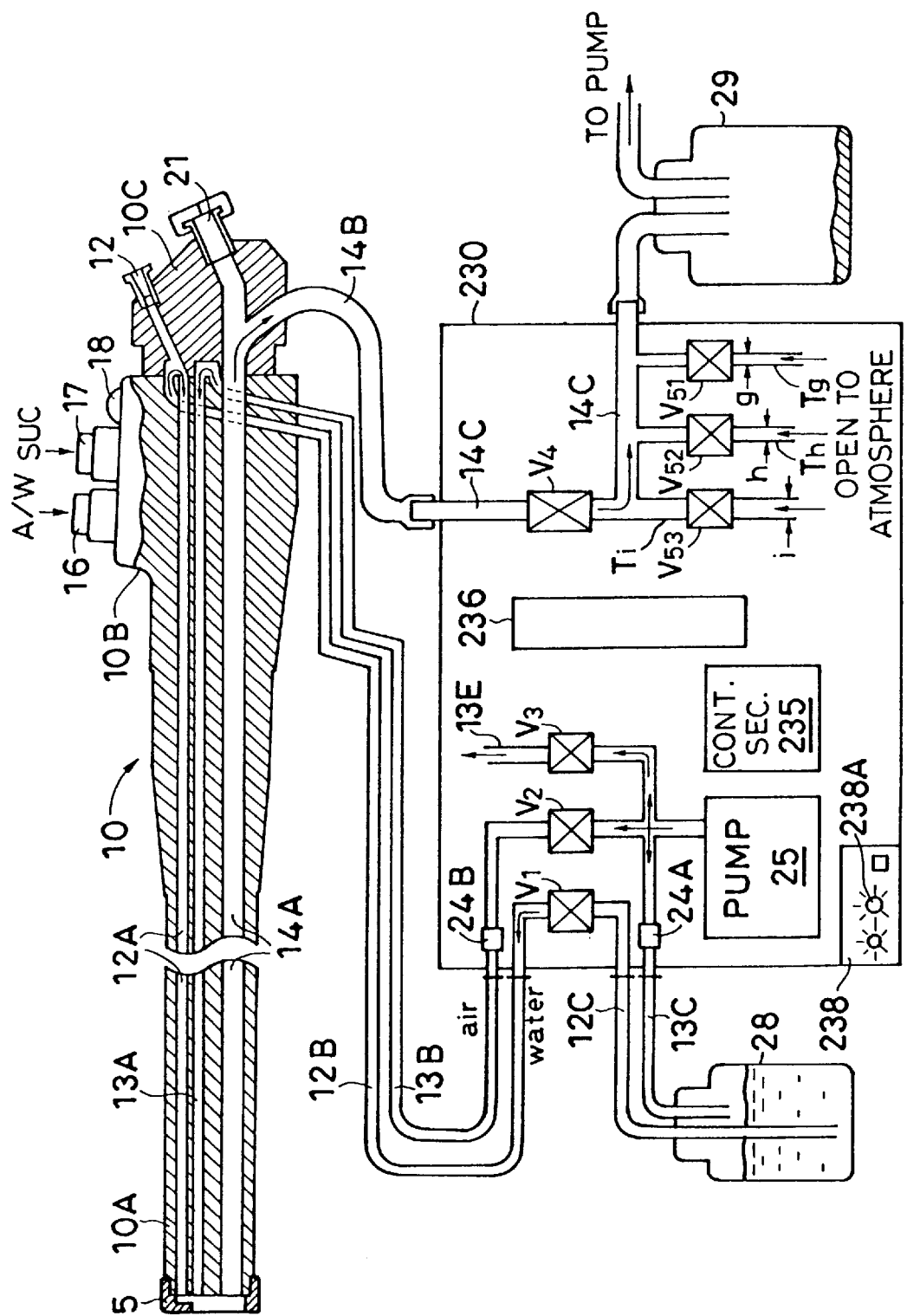
FIG. 8 is a schematic view showing a configuration of a flow rate controller for an endoscope pipe in accordance with a fourth embodiment of the present invention.

FIG. 8 shows a configuration of a flow rate controller for an endoscope pipe in accordance with a fourth embodiment. As shown in FIG. 8, the configuration of an endoscope 10 is the same as that of the third embodiment. As in the case of the first embodiment, an electromagnetic valve unit 230 of the fourth embodiment is provided with electromagnetic valves V1, V2 and V3 for opening/closing a water feed pipe (pipe) 12 and an air feed pipe (pipe) 13, and check valves 24A and 24B, and also provided with a pump 25, a feed water tank 28, a control section 235, and a power source 236.

Further, there are provided a suction pipe 14C connected to a suction pipe 14B and an electromagnetic valve V4, and this suction pipe 14C is connected with a suction tank 29 communicating with a pump (not shown). In order to control the flow rate of the suction pipe (pipe) 14, there are provided three open-to-atmosphere pipes Tg, Th and Ti and electromagnetic valves V51, V52 and V53. Specifically, the pipes Tg, Th and Ti whose pipe diameters (inside diameters) g, h and i are set in the size relationship of g<h<i are disposed branching from the suction pipe 14C, and the electromagnetic valves V51, V52 and V53 are installed in the pipes Tg, Th and Ti, respectively.

Also, a flow rate regulating switch section 238 for as regulating the flow rate of suction is provided on the control panel of the electromagnetic valve unit 230, and by the operation of a suction flow rate switch 238A in the flow rate regulating switch section 238, the suction flow rate can be controlled in a stepwise manner.

The following is a description of the operation of the fourth embodiment configured as described above. When the suction switch 17 is operated, the electromagnetic valve V4 is opened, and the opening/closing control of the electromagnetic valves V51, V52 and V53 is carried out so that the flow rate becomes a value set in the flow rate regulating switch section 238. Specifically, in this embodiment, since the open-to-atmosphere pipes Tg, Th and Ti with three different diameters are used, taking the reference flow rates of the pipes with diameters of g, h and i as Hg, Hh and Hi, eight stages of atmosphere suction flow rates of, for example, 0 (in the case where all of the electromagnetic valves V51, V52 and V53 are closed)<Hg<Hh<Hi<Hg+Hh<Hg+Hi<Hh+Hi<Hg+Hh+Hi (other magnitude relationships may be used) can be set including the combination of pipes.

In this case, the higher the atmosphere suction flow rate is, the lower the suction flow rate is. If all of the electromagnetic valves V51, V52 and V53 are closed, the maximum suction flow rate is set, while if all of the electromagnetic valves V51, V52 and V53 are opened, the minimum suction flow rate is set.

Figure 9:
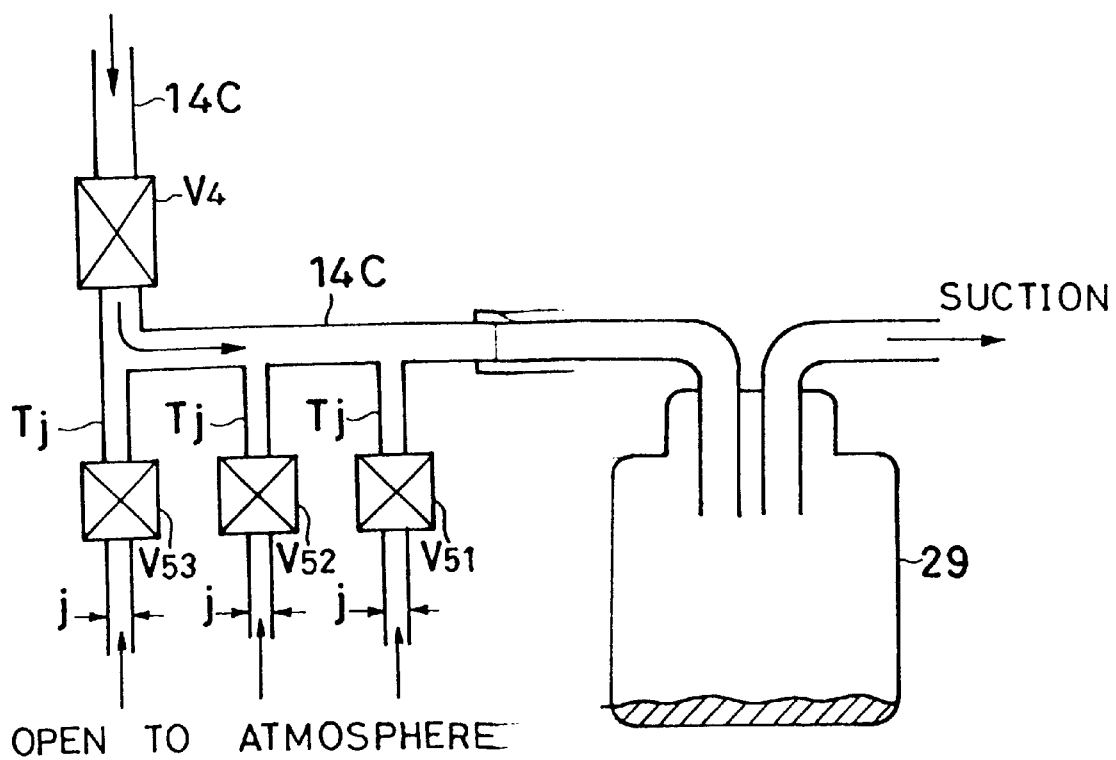
FIG. 9 is a schematic view showing another configuration for regulating the suction flow rate in the fourth embodiment.
Figure 10:
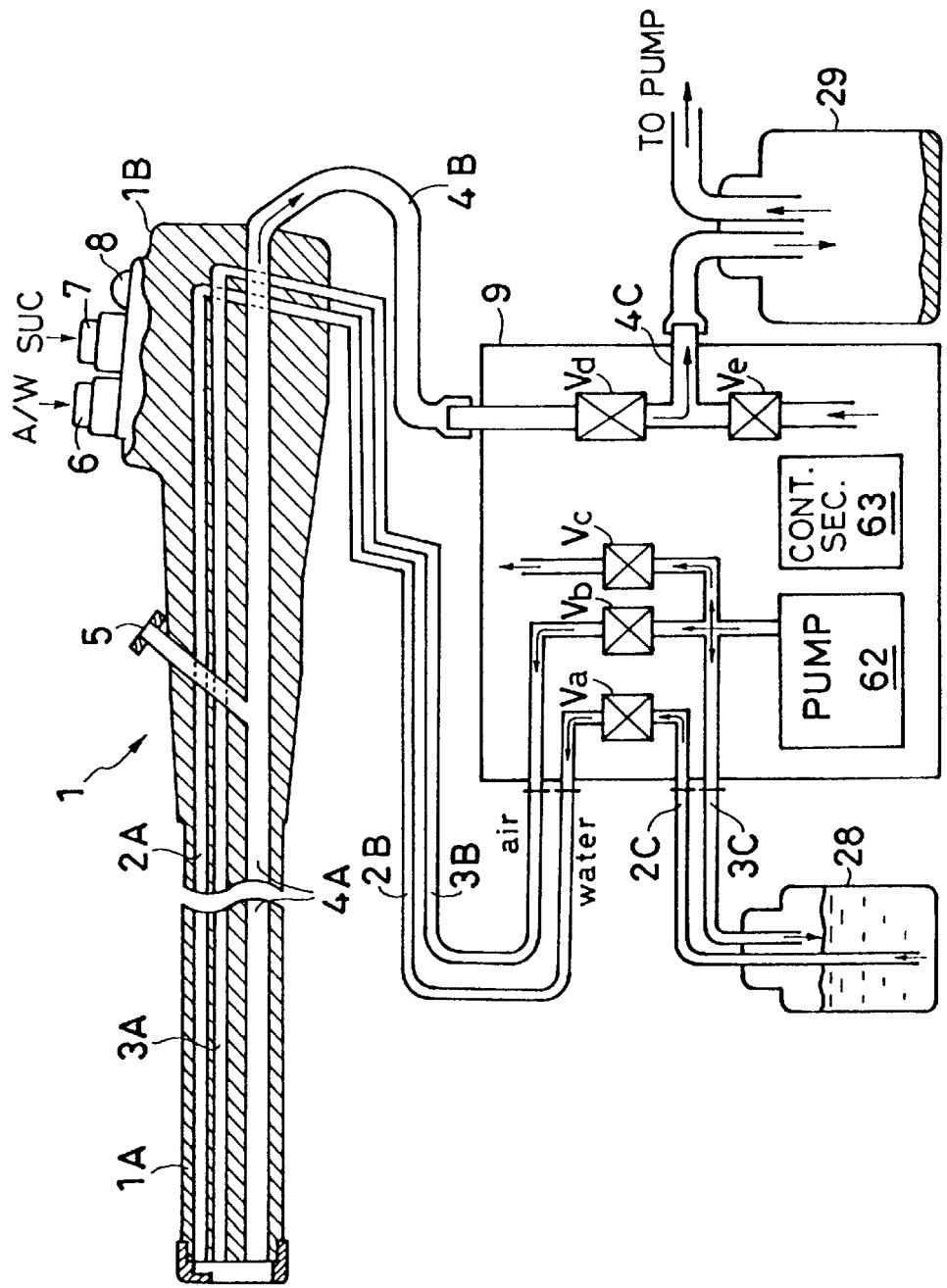
FIG. 10 is a schematic view showing a configuration of a conventional pipe system and fluid controller for an endoscope.

FIG. 9 shows another configuration for regulating the suction flow rate. In this case, the inside diameters of the plural open-to-atmosphere pipes are equal. Specifically, as shown in FIG. 9, three branching open-to-atmosphere pipes Tj are installed to the suction pipe 224C, and these pipes Tj have the same inside diameter j. In this embodiment, taking the reference flow rate of pipe as Hj, four stages of atmosphere suction flow rate of, for example, the case where all of the electromagnetic valves V51, V52 and V53 are closed<Hj<2HJ<3Hj can be set including the combination of pipes, whereby the suction flow rate can be regulated variably.

In this embodiment as well, the flow rate operation can be performed by the operation switch 141 shown in FIG. 7 which is disposed in the operating section 10B of endoscope in place of the suction switch 17. According to this configuration, the pressing force of the operating body 141A is detected in a stepwise value, and the opening/closing of the electromagnetic valves V51, V52, and V53 is controlled according to this stepwise operating pressure, by which the flow rate can be regulated variably in a stepwise manner.

As described above, according to the fourth embodiment, the fluid flow rate in the suction pipe can be regulated variably, so that the discharge of content according to the situation while considering the effect on the inside of a body being observed and the like is enabled. As a result, the burden on the patient is alleviated, and an endoscope which is easy to use can be obtained.

Also, by regulating the flow rate by combining plural open-to-atmosphere pipes, the flow rate can be set finely, and further the flow rate control can be carried out easily by using the operation switch in the operating section of endoscope.

What is claimed is:

1. A flow rate controller for an endoscope pipe comprising:

at least one pipe provided in an endoscope;

a plurality of control pipes with different pipe diameters connected to the at least one pipe in a branching state;

an opening/closing valve operably connected to each of the plurality of control pipes for opening/closing each of the plural control pipes; and a control section for variably regulating the flow rate in the at least one pipe by selective opening/closing control of the plural opening/closing valves.

2. A flow rate controller for an endoscope pipe according to claim 1, wherein the flow rate is variably regulated by the combined use of the plural control pipes on the basis of the control of the plural opening/closing valves.

3. A flow rate controller for an endoscope pipe according to claim 1, wherein an operation switch for regulating the flow rate is disposed on the side of a fluid control unit separate from the endoscope.

4. A flow rate controller for an endoscope pipe according to claim 1, wherein the flow rate is regulated by means of an operation switch provided in an operating section of the endoscope.

5. A flow rate controller for an endoscope pipe according to claim 1, wherein when all of the plural control pipes are shut off simultaneously, flow is completely stopped in the at least one pipe.

6. A flow rate controller for an endoscope pipe comprising:

a suction pipe provided in an endoscope;

a plurality of open-to-atmosphere pipes connected to the suction pipe in a branching state;

plural opening/closing valves operably connected to each of the plurality of open-to-atmosphere pipes for opening/closing each of the plural open-to-atmosphere pipes; and a control section for variably regulating the flow rate in the suction pipe by selective opening/closing control of the plural opening/closing valves, and wherein pipes with different inside diameters are used as the plural open-to-atmosphere pipes.

7. A flow rate controller for an endoscope pipe according to claim 6, wherein the flow rate is variably regulated by the combined use of the plural open-to-atmosphere pipes on the basis of the control of the plural opening/closing valves.

8. A flow rate controller for an endoscope pipe according to claim 6, wherein an operation switch for regulating the flow rate is disposed on the side of a fluid control unit separate from the endoscope.

9. A flow rate controller for an endoscope pipe according to claim 6, wherein the flow rate is regulated by means of an operation switch provided in an operating section of the endoscope.

* * * * *